(12) United States Patent
Bi

(10) Patent No.: US 8,156,798 B1
(45) Date of Patent: Apr. 17, 2012

(54) HIGH PRESSURE HIGH TEMPERATURE FLUID DENSITOMETER

(76) Inventor: Hongfeng Bi, Houston, TX (US)

(*) Notice: Subject to any disclaimer, the term of this patent is extended or adjusted under 35 U.S.C. 154(b) by 0 days.

(21) Appl. No.: 12/833,723

(22) Filed: Jul. 9, 2010

(51) Int. Cl.
G01F 17/00 (2006.01)
G01F 19/00 (2006.01)

(52) U.S. Cl. ............................................. 73/149; 73/426

(58) Field of Classification Search .................... 73/149, 73/168
See application file for complete search history.

(56) References Cited

U.S. PATENT DOCUMENTS

| | | | |
|---|---|---|---|
| 2,981,111 A | 4/1961 | McIlwraith et al. | |
| 3,129,585 A | 4/1964 | Hamilton | |
| 3,574,281 A | 4/1971 | Casey et al. | |
| 5,159,828 A | 11/1992 | Steiger et al. | |
| 6,234,061 B1* | 5/2001 | Glasson | 92/5 R |
| 6,718,281 B2 | 4/2004 | Duncan et al. | |
| 6,817,238 B2 | 11/2004 | Go Boncan et al. | |
| 6,918,292 B2 | 7/2005 | Go Boncan et al. | |
| 7,240,545 B1 | 7/2007 | Jennings | |
| 7,287,416 B1 | 10/2007 | Bi | |
| 7,290,476 B1* | 11/2007 | Glasson | 92/5 R |
| 7,377,333 B1* | 5/2008 | Sugiura | 175/45 |
| 7,412,877 B1 | 8/2008 | Bi | |
| 7,982,459 B2* | 7/2011 | Killian et al. | 324/240 |
| 2001/0018861 A1* | 9/2001 | Glasson | 92/5 R |
| 2003/0029310 A1* | 2/2003 | Glasson | 92/5 R |
| 2004/0050439 A1* | 3/2004 | Weber | 138/30 |
| 2006/0144217 A1* | 7/2006 | Neumann | 91/1 |
| 2006/0236539 A1* | 10/2006 | Glasson | 29/890.06 |
| 2008/0190104 A1* | 8/2008 | Bresie | 60/476 |
| 2010/0050863 A1* | 3/2010 | Wenker et al. | 92/5 R |
| 2010/0161184 A1* | 6/2010 | Marathe et al. | 701/50 |
| 2010/0307233 A1* | 12/2010 | Glasson et al. | 73/168 |

* cited by examiner

Primary Examiner — Lisa Caputo
Assistant Examiner — Jamel Williams

(57) ABSTRACT

A method and apparatus for monitoring liquid volume change consists of a cylindrical cell assembly (80) capable of withstanding high pressure and high temperature with a sealed movable piston (24) separating a pressurization fluid (11) from a sample (25). A top magnet (72) moves with piston (24) and its movement is measured by a magnetometer (10). Heat is provided via a heater (52) and pressure is controlled via pressurization fluid (11).

20 Claims, 4 Drawing Sheets

US 8,156,798 B1

HIGH PRESSURE HIGH TEMPERATURE FLUID DENSITOMETER

CROSS-REFERENCE TO RELATED APPLICATIONS

None.

BACKGROUND

1. Field of Invention

The present invention relates to apparatuses and methods for monitoring, measuring, or analyzing changes in the volume and/or density of solid and/or fluid samples.

2. Description of Prior Art

In many industrial environments—including but not limited to the drilling of oil and geothermal wells—the use of fluids under high temperature and high pressure conditions is commonplace. Understanding and predicting the changes of said fluids under said conditions can be vital to their efficient and safe use; in particular, changes of their density or specific volume.

Devices that can be found within the marketplace that are capable of resolving changes of specific volume are densitometers, pycnometers, dilatometers, pressure-volume-temperature (pvT) devices, etc.

U.S. Pat. No. 6,718,281 describes a dilatometer that can measure volume changes of liquid and solid samples. However, it possesses multiple disadvantages such as excessively complicated mechanical structure, usage of highly dangerous and toxic mercury, the fact that it is not capable of being pressurized to very high pressure due to its optical components, etc. These disadvantages prevent it from being used to monitor fluid and solid density changes under simulated drilling conditions.

Other devices which are used to measure the volume change of fluids, such as the pycnometer shown in U.S. Pat. No. 3,129,585, use mechanical indicators to measure the density change of a fluid, without the capability of recording data. Also, in FIG. 1 of U.S. Pat. No. 3,129,585, the movement of piston 14 has to be mechanically transferred to the outside of a pressurized chamber through a seal. This would induce measurement errors and introduce difficulty in sealing when pressure is above 10,000 psi.

It is an object of this invention to provide a means for testing liquid density changes under simulated downhole conditions in deep oil or geothermal wells.

It is a further object of this invention to provide a means for testing the volumetric expansion or contraction of a solid sample under varying and controllable conditions of temperature and pressure without contamination by pressurization fluid.

It is a further object of this invention to provide a means for automatically tracking and recording said changes in sample volume.

It is another object of this invention to provide a densitometer which does not require the use of any specific fluid of any toxicity whatsoever.

It is another object of this invention to provide a specific volume measurement device which requires substantially less maintenance work than other designs yet meets industry standards of accuracy, reliability, durability, dependability, and ease of cleaning.

SUMMARY OF THE PRESENT INVENTION

A densitometer in accord with the present invention is comprised of a cylindrical pressure cell capable of withstanding high pressure and high temperature. The pressure cell consists of a body and a cap. A heater is positioned radially around the bottom of the pressure cell. The interior chamber of the pressure cell is divided into an upper and a lower section by a sealed piston. Said sealed piston is capable of vertical movement inside of the pressure cell.

In the preferred embodiment, a magnetometer is positioned directly above the pressure cell. The upper section of the pressure cell also contains a magnet attached to the top of said sealed piston so that as the piston changes position vertically, the distance from the magnet to the magnetometer changes correspondingly. This piston movement is transferred to specific volume changes mathematically and is digitally recorded.

Pressure is applied to the top of the piston via pressurization fluid injected into the upper section of the pressure cell. A fluid sample and/or a solid sample immersed in a fluid sample is contained in the lower section of the pressure cell, and the expansion or contraction of said solid and/or fluid samples forces the piston to move.

In the preferred embodiment, a stirring magnet is placed around a Rulon or plastic bushing which is mounted on a pivot inside of the pressure cell, and said magnet is rotated by a magnet mount located outside the pressure cell.

DRAWING FIGURES

Other objects, features and advantages will be apparent from the following detailed descriptions of preferred embodiments taken in conjunction with accompanying drawings in which.

REFERENCE NUMERALS IN DRAWINGS

Figure 1:
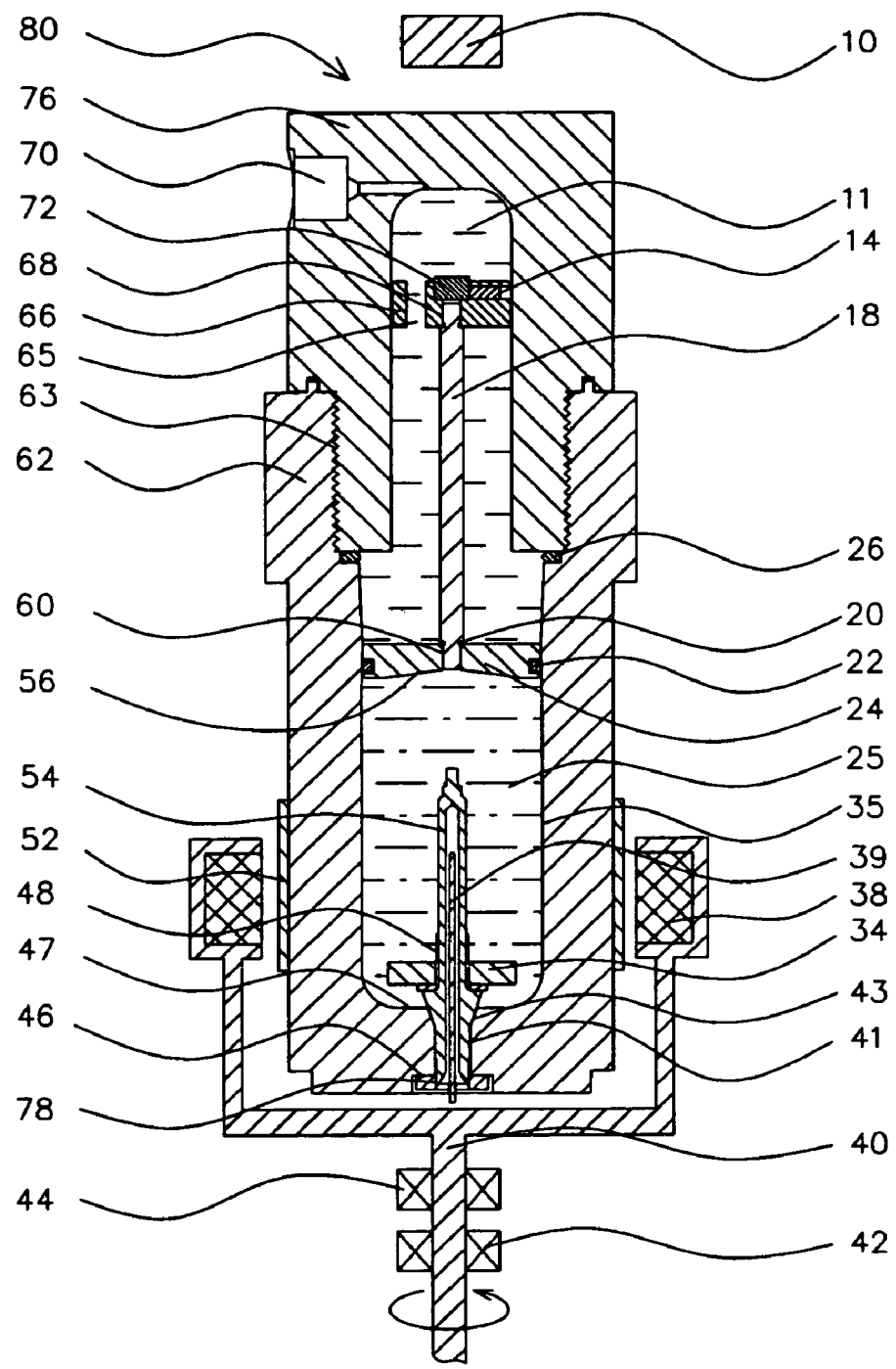
FIG. 1 is a cross-section view of cell assembly 80 in the preferred embodiment of the invention.

| 10  | magnetometer         | 10A | magnetometer         |
|-----|----------------------|-----|----------------------|
| 10B | magnetometer         | 10C | magnetometer         |
| 11  | pressurization fluid | 11A | pressurization fluid |
| 11B | pressurization fluid | 11C | pressurization fluid |
| 14  | set screw            | 14B | set screw            |
| 18  | rod                  | 18B | rod                  |
| 18C | rod                  | 20  | o-ring               |
| 20A | o-ring               | 20B | o-ring               |
| 20C | o-ring               | 22  | o-ring               |
| 22A | o-ring               | 22B | o-ring               |
| 22C | o-ring               | 24  | piston               |
| 24A | piston               | 24B | piston               |
| 24C | piston               | 25  | sample               |
| 25A | sample               | 25B | sample               |
| 25C | sample               | 26  | o-ring               |
| 26A | o-ring               | 26B | o-ring               |
| 26C | o-ring               | 28A | adapter              |
| 34  | coupling magnet      | 34A | coupling magnet      |
| 35  | cell wall            | 35A | cell wall            |
| 35B | cell wall            | 35C | cell wall            |
| 36B | solid sample         | 37B | seal plug            |
| 38  | drive magnet         | 38A | drive magnet         |
| 39  | thermal couple       | 39A | thermal couple       |
| 39B | thermal couple       | 39C | thermal couple       |
| 40  | magnet mount         | 40A | magnet mount         |
| 41  | straight bore        | 41A | straight bore        |

-continued

| | | | |
|---|---|---|---|
| 41B | straight bore | 41C | straight bore |
| 42 | bearing | 42A | bearing |
| 43 | conical surface | 43A | conical surface |
| 43B | conical surface | 43C | conical surface |
| 44 | bearing | 44A | bearing |
| 46 | lock nut | 46A | lock nut |
| 46B | lock nut | 46C | lock nut |
| 47 | cell bottom | 47A | cell bottom |
| 47B | cell bottom | 47C | cell bottom |
| 48 | bushing | 48A | bushing |
| 52 | heater | 52A | heater |
| 52B | heater | 52C | heater |
| 54 | pivot | 54A | pivot |
| 54C | pivot | 56 | conical surface |
| 56A | conical surface | 56B | conical surface |
| 56C | conical surface | 58A | o-ring |
| 59A | conical surface | 60 | screw thread |
| 60A | screw thread | 60B | screw thread |
| 60C | screw thread | 62 | cell body |
| 62A | cell body | 62B | cell body |
| 62C | cell body | 63 | screw thread |
| 63A | screw thread | 63B | screw thread |
| 63C | screw thread | 64A | screw |
| 65 | hole | 65B | hole |
| 66 | magnet holder | 66B | magnet holder |
| 66C | magnet holder | 68 | screw thread |
| 68B | screw thread | 68C | screw thread |
| 70 | pressurization port | 70A | pressurization port |
| 70B | pressurization port | 70C | pressurization port |
| 72 | top magnet | 72A | top magnet |
| 72B | top magnet | 72C | top magnet |
| 74C | o-ring | 76 | cell cap |
| 76A | cell cap | 76B | cell cap |
| 76C | cell cap | 78 | thread |
| 78A | thread | 78B | thread |
| 78C | thread | 80 | cell assembly |
| 80A | cell assembly | 80B | cell assembly |
| 80C | cell assembly | | |

Description—FIG. 1—Preferred Embodiment

FIG. 1 is a cross-section view of a cell assembly 80 with a cell body 62 and a cell cap 76. Cell body 62 is detachable from cell cap 76 via a screw thread 63. An o-ring 26 assures against leakage through screw thread 63. Inside of cell body 62 and below screw thread 63 is a cell wall 35, which is cylindrical and extends downward to a cell bottom 47. A tapered hole with a conical surface 43 and a straight bore 41 is located in the center of cell bottom 47. Cell body 62 is mostly filled with a sample 25. A pivot 54, which is secured to cell bottom 47 by a lock nut 46 via a thread 78, is seated into said tapered hole on conical surface 43. Lock nut 46 is tightened to provide initial seal on conical surface 43 between cell bottom 47 and pivot 54. A thermal couple 39 is inserted into the center of pivot 54.

Radially outward of the outer surface of pivot 54 is a bushing 48. Bushing 48 is made of Rulon, Teflon or an equivalent plastic. Radially outward of bushing 48 is a coupling magnet 34, which can rotate freely on the same central axis of pivot 54. A magnet mount 40 is rotationally supported on the outside of cell body 62 by a bearing 42 and a bearing 44. Magnet mount 40 can be rotated by any conventional means such as gear box or motor. A drive magnet 38 is mounted on magnet mount 40 at the same level where coupling magnet 34 is mounted inside of cell body 62.

A piston 24 is attached to the lower end of a rod 18 by a screw thread 60, with a conical surface 56 facing down. An o-ring 22 is mounted onto piston 24 and an o-ring 20 is mounted onto rod 18 to assure against the mixing of sample 25 with a pressurization fluid 11. The top of rod 18 is attached to a magnet holder 66 by a screw thread 68.

A top magnet 72 is fixed to magnet holder 66 by a set screw 14. A pressurization port 70 is provided to supply pressurization fluid 11 to the top of piston 24. Said pressurization fluid 11 is able to flow through magnet holder 66 through a hole 65. A magnetometer 10 is positioned above the top of cell assembly 80. A heater 52 heats cell body 62 while thermal couple 39 provides temperature feedback for temperature control.

Operation—FIG. 1—Preferred Embodiment

In FIG. 1, place pivot 54 inside of cell body 62 so that straight bore 41 and conical surface 43 are secured to cell bottom 47 via thread 78 and lock nut 46. Pivot 54 can be cleaned together with cell body 62. Fit bushing 48 over pivot 54. Fit coupling magnet 34 onto pivot 54 on top of bushing 48. Due to the magnetic coupling between drive magnet 38 and coupling magnet 34, coupling magnet 34 is able to rotate at the same revolving speed as magnet mount 40 does.

Pour sample 25 into cell body 62 so that the top surface of sample 25 submerges the top of pivot 54 enough so that piston 24 has enough upward and downward movement range. Install o-ring 22 onto piston 24 and push piston 24 downward into cell body 62. As piston 24 is pushed down, o-ring 22 forms a seal with cell wall 35, and conical surface 56 at the bottom of piston 24 ensures that air is first funneled out through the center of piston 24. Keep pushing down on piston 24 until sample 25 comes out at the center of piston 24. Install o-ring 20 onto rod 18 above screw thread 60, then screw rod 18 into piston 24 via screw thread 60. Screw magnet holder 66 onto rod 18 via screw thread 68. Attach top magnet 72 to magnet holder 66 and secure it via set screw 14. Install o-ring 26 into cell body 62 below screw thread 63.

Screw cell cap 76 onto cell body 62 via screw thread 63, forming cell assembly 80. Heater 52 heats cell body 62 while thermal couple 39 provides temperature feedback for temperature control.

Pressurization fluid 11 is introduced into cell top chamber via pressurization port 70, flowing through hole 65 in magnet holder 66, compressing sample 25 inside of cell body 62 through the movement of piston 24. Magnet mount 40 is driven to rotate on bearing 44 and bearing 42 at desired speed, carrying drive magnet 38 and causing coupling magnet 34 to rotate as well, which provides stirring of sample 25. The stirring motion provided by the rotation of coupling magnet 34 helps to maintain sample 25 temperature consistency.

The temperature and pressure conditions inside of cell assembly 80 cause sample 25 density to change, which in turn moves piston 24. Top magnet 72 moves with piston 24. The movement of top magnet 72 is sensed by magnetometer 10 and is translated to density change of sample 25 mathematically.

Figure 2:
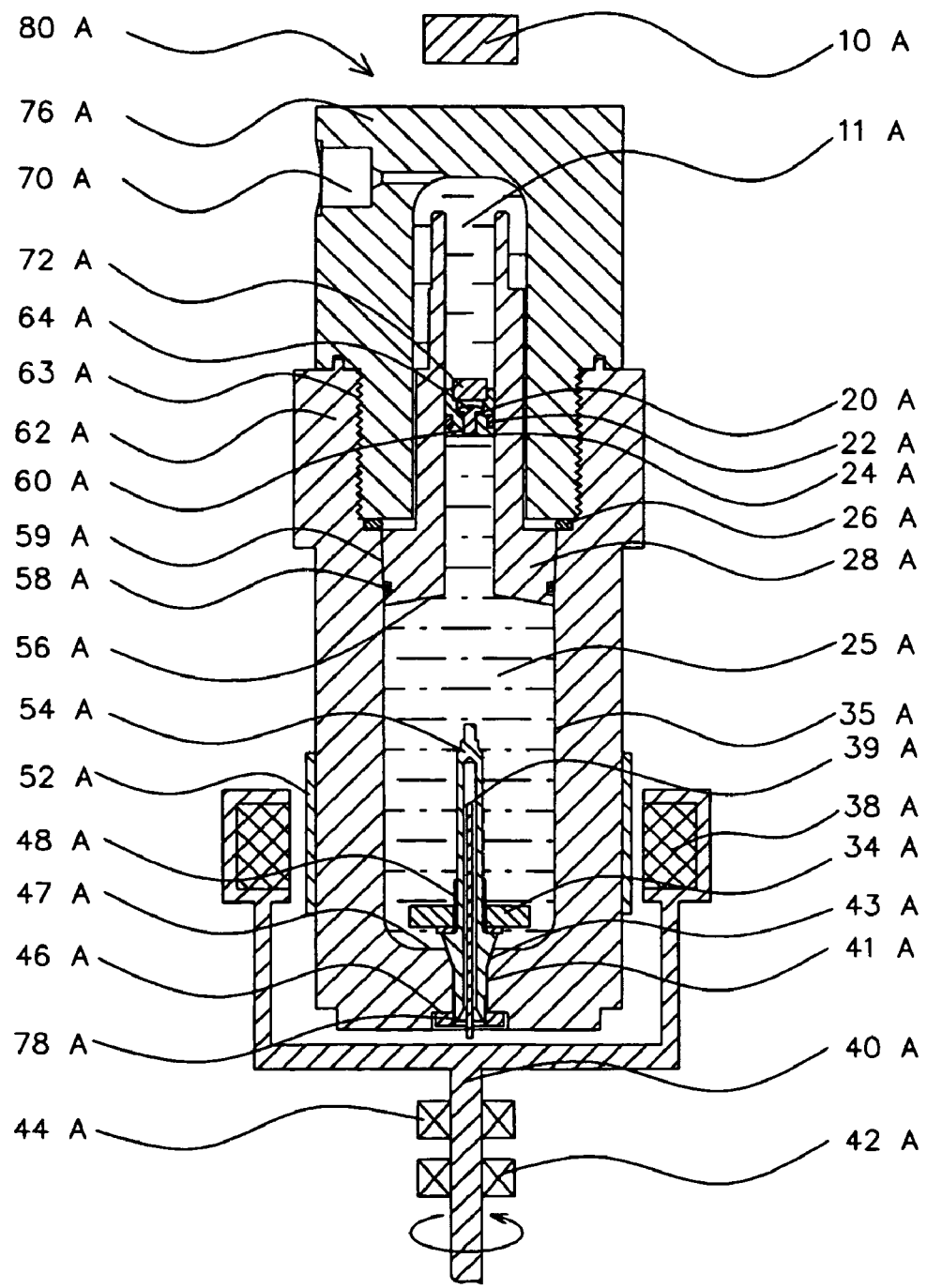
FIG. 2 is an alternative configuration of cell assembly 80A with a different piston configuration.

Description—FIG. 2—An Alternative Cell Assembly Embodiment with Different Piston Configuration FIG. 2 is a cross-section view of a cell assembly 80A with a cell body 62A and a cell cap 76A. Cell body 62A is detachable from cell cap 76A via a screw thread 63A. An o-ring 26A assures against leakage through screw thread 63A. Inside of cell body 62A and below screw thread 63A is a cell wall 35A, which is cylindrical and extends downward to a cell bottom 47A. A tapered hole with a conical surface 43A and a straight bore 41A is located in the center of cell bottom 47A. Cell body 62A is mostly filled with a sample 25A. A pivot 54A, which is secured to cell bottom 47A by a lock nut 46A via a thread 78A, is seated into said tapered hole on conical surface 43A. Lock nut 46A is tightened to provide initial seal on conical surface 43A between cell bottom 47A and pivot 54A. A thermal couple 39A is inserted into the center of pivot 54A.

Radially outward of the outer surface of pivot 54A is a bushing 48A. Bushing 48A is made of Rulon, Teflon or an equivalent plastic. Radially outward of bushing 48A is a coupling magnet 34A, which can rotate freely on the same central axis of pivot 54A. A magnet mount 40A is rotationally supported on the outside of cell body 62A by a bearing 42A and a bearing 44A. Magnet mount 40A can be rotated by any conventional means such as gear box or motor. A drive magnet 38A is mounted on magnet mount 40A at the same level where coupling magnet 34A is mounted inside of cell body 62A.

An adapter 28A with a conical surface 56A at the lower end is situated inside of cell body 62A so that an o-ring 58A, which is installed on adapter 28A, rests on a conical surface 59A and assures against the contamination of sample 25A with a pressurization fluid 11A.

A piston 24A is placed inside of adapter 28A. An o-ring 22A is installed into a groove on the outside of piston 24A. An o-ring 20A is installed onto a screw 64A. Screw 64A is then installed into piston 24A via a screw thread 60A. A top magnet 72A is placed into the top of piston 24A.

A pressurization port 70A is provided to supply pressurization fluid 11A to the top of piston 24A. A magnetometer 10A is positioned above the top of cell assembly 80A. A heater 52A heats cell body 62A while thermal couple 39A provides temperature feedback for temperature control.

Operation—FIG. 2—An Alternative Cell Embodiment with Different Piston Configuration In FIG. 2, place pivot 54A inside of cell body 62A so that straight bore 41A and conical surface 43A are secured to cell bottom 47A via thread 78A and lock nut 46A. Pivot 54A can be cleaned together with cell body 62A. Fit bushing 48A over pivot 54A. Fit coupling magnet 34A onto pivot 54A on top of bushing 48A. Due to the magnetic coupling between drive magnet 38A and coupling magnet 34A, coupling magnet 34A is able to rotate at the same revolving speed as magnet mount 40A does.

Install o-ring 58A onto adapter 28A, and place adapter 28A into cell body 62A so that o-ring 58A rests and forms a seal on conical surface 59A above cell wall 35A. Inject sample 25A into cell body 62A through the center of adapter 28A, so that the top surface of sample 25A submerges conical surface 56A and fills the center of adapter 28A without overflowing the top of adapter 28A. Install o-ring 22A onto piston 24A. Push piston 24A down into the center of adapter 28A until sample 25A begins to drain through the center hole in piston 24A. Install o-ring 20A onto screw 64A. Install screw 64A into the center of piston 24A via screw thread 60A. Drop top magnet 72A into the top of piston 24A. Install o-ring 26A onto cell body 62A below screw thread 63A.

Screw cell cap 76A onto cell body 62A via screw thread 63A, forming cell assembly 80A. Heater 52A heats cell body 62A while thermal couple 39A provides temperature feedback for temperature control.

Pressurization fluid 11A is introduced into cell top chamber via pressurization port 70A, compressing sample 25A inside of cell body 62A through the movement of piston 24A. O-ring 20A and o-ring 22A assure against contamination of sample 25A with pressurization fluid 11A. Magnet mount 40A is driven to rotate on bearing 44A and bearing 42A at desired speed, carrying drive magnet 38A and causing coupling magnet 34A to rotate as well, which provides stirring of sample 25A. The stirring motion provided by the rotation of coupling magnet 34A helps to maintain sample 25A temperature consistency.

The temperature and pressure conditions inside of cell assembly 80A cause sample 25A density to change, which in turn moves piston 24A. Top magnet 72A moves with piston 24A. The movement of top magnet 72A is sensed by magnetometer 10A and is translated to density change of sample 25A mathematically.

Figure 3:
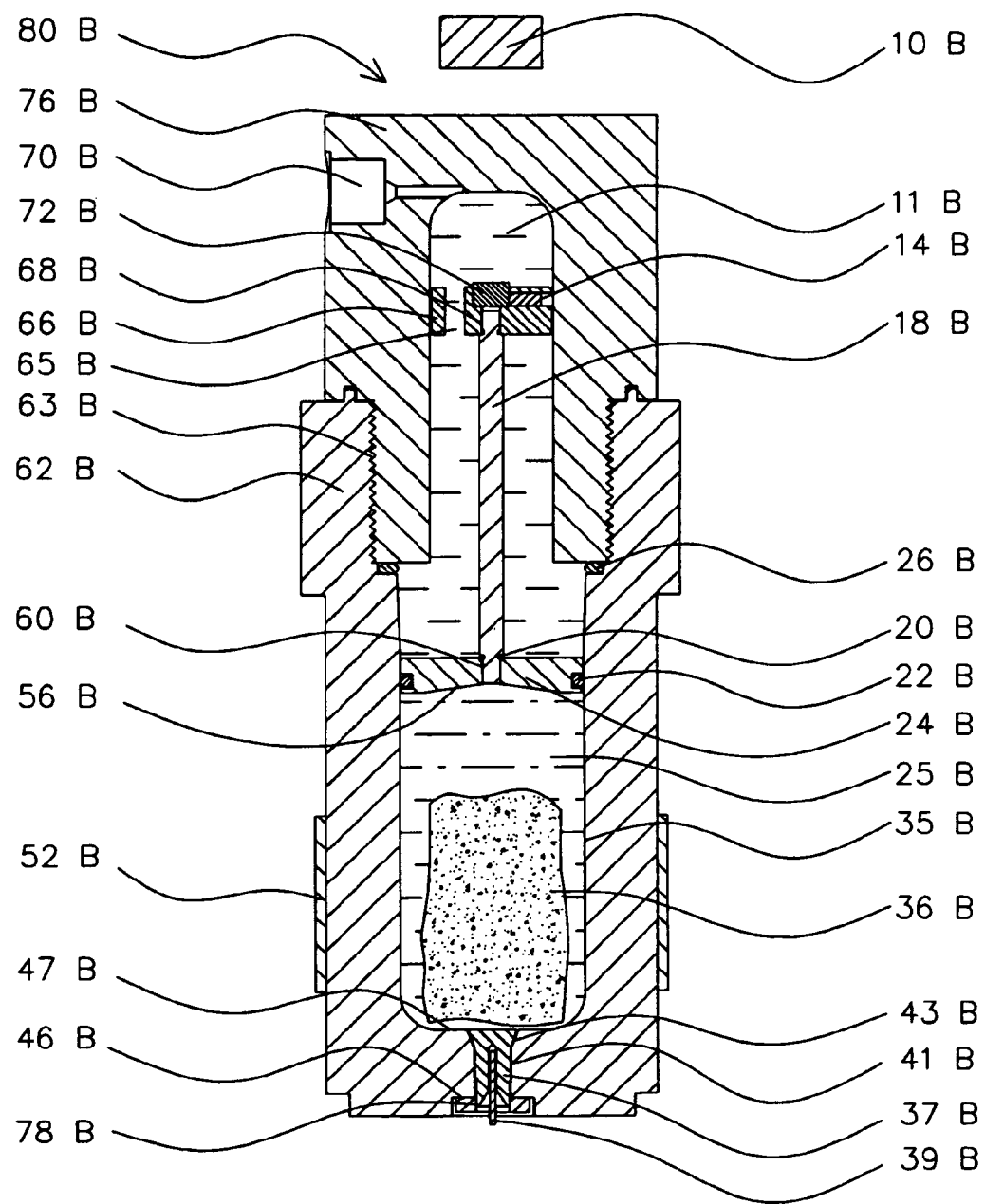
FIG. 3 shows an alternative configuration of cell assembly 80B to allow the testing of a solid sample.

Description—FIG. 3—An Alternative Cell Assembly Embodiment Configured to Measure Solid Samples FIG. 3 is a cross-section view of a cell assembly 80B with a cell body 62B and a cell cap 76B. Cell body 62B is detachable from cell cap 76B via a screw thread 63B. An o-ring 26B assures against leakage through screw thread 63B. Inside of cell body 62B and below screw thread 63B is a cell wall 35B, which is cylindrical and extends downward to a cell bottom 47B. A tapered hole with a conical surface 43B and a straight bore 41B is located in the center of cell bottom 47B. Cell body 62B is mostly filled with a sample 25B surrounding a solid sample 36B. A seal plug 37B, which is secured to cell bottom 47B by a lock nut 46B via a thread 78B, is seated into said tapered hole on conical surface 43B. Lock nut 46B is tightened to provide initial seal on conical surface 43B between cell bottom 47B and seal plug 37B. A thermal couple 39B is inserted into the center of seal plug 37B.

A piston 24B is attached to the lower end of a rod 18B by a screw thread 60B, with a conical surface 56B facing down. An o-ring 22B is mounted onto piston 24B and an o-ring 20B is mounted onto rod 18B to assure against the mixing of sample 25B with a pressurization fluid 11B. The top of rod 18B is attached to a magnet holder 66B by a screw thread 68B. A top magnet 72B is fixed to magnet holder 66B by a set screw 14B. A pressurization port 70B is provided to supply pressurization fluid 11B to the top of piston 24B. Said pressurization fluid 11B is able to flow through magnet holder 66B through a hole 65B. A magnetometer 10B is positioned above the top of cell assembly 80B. A heater 52B heats cell body 62B while thermal couple 39B provides temperature feedback for temperature control.

Operation—FIG. 3—An Alternative Cell Assembly Embodiment Configured to Measure solid samples In FIG. 3, place seal plug 37B inside of cell body 62B so that straight bore 41B and conical surface 43B are secured to cell bottom 47B via thread 78B and lock nut 46B. Seal plug 37B can be cleaned together with cell body 62B.

Place solid sample 36B into cell body 62B. Pour sample 25B into cell body 62B so that the surface of sample 25B substantially submerges the top of solid sample 36B and piston 24B has enough upward and downward movement range.

Install o-ring 22B onto piston 24B and push piston 24B downward into cell body 62B. As piston 24B is pushed down, o-ring 22B forms a seal with cell wall 35B, and conical surface 56B at the bottom of piston 24B ensures that air is first funneled out through the center of piston 24B. Keep pushing down on piston 24B until sample 25B comes out at the center of piston 24B. Install o-ring 20B onto rod 18B above screw thread 60B, then screw rod 18B into piston 24B via screw thread 60B. Screw magnet holder 66B onto rod 18B via screw thread 68B. Attach top magnet 72B to magnet holder 66B and secure it via set screw 14B. Install o-ring 26B into cell body 62B.

Screw cell cap 76B onto cell body 62B via screw thread 63B, forming cell assembly 80B. Heater 52B heats cell body 62B while thermal couple 39B provides temperature feedback for temperature control.

Pressurization fluid 11B is introduced into cell top chamber via pressurization port 70B, flowing through hole 65B in magnet holder 66B, compressing sample 25B and solid sample 36B inside of cell body 62B through the movement of piston 24B. O-ring 20B and o-ring 22B assure against contamination of sample 25B with pressurization fluid 11B.

The temperature and pressure conditions inside of cell assembly 80B cause sample 25B and solid sample 36B density to change. The combined volume changes of sample 25B and solid sample 36B moves piston 24B. Top magnet 72B moves with piston 24B. The movement of top magnet 72B is sensed by magnetometer 10B and translated to density change of solid sample 36B mathematically, with the prior knowledge of sample 25B density changes under current testing conditions.

Figure 4:
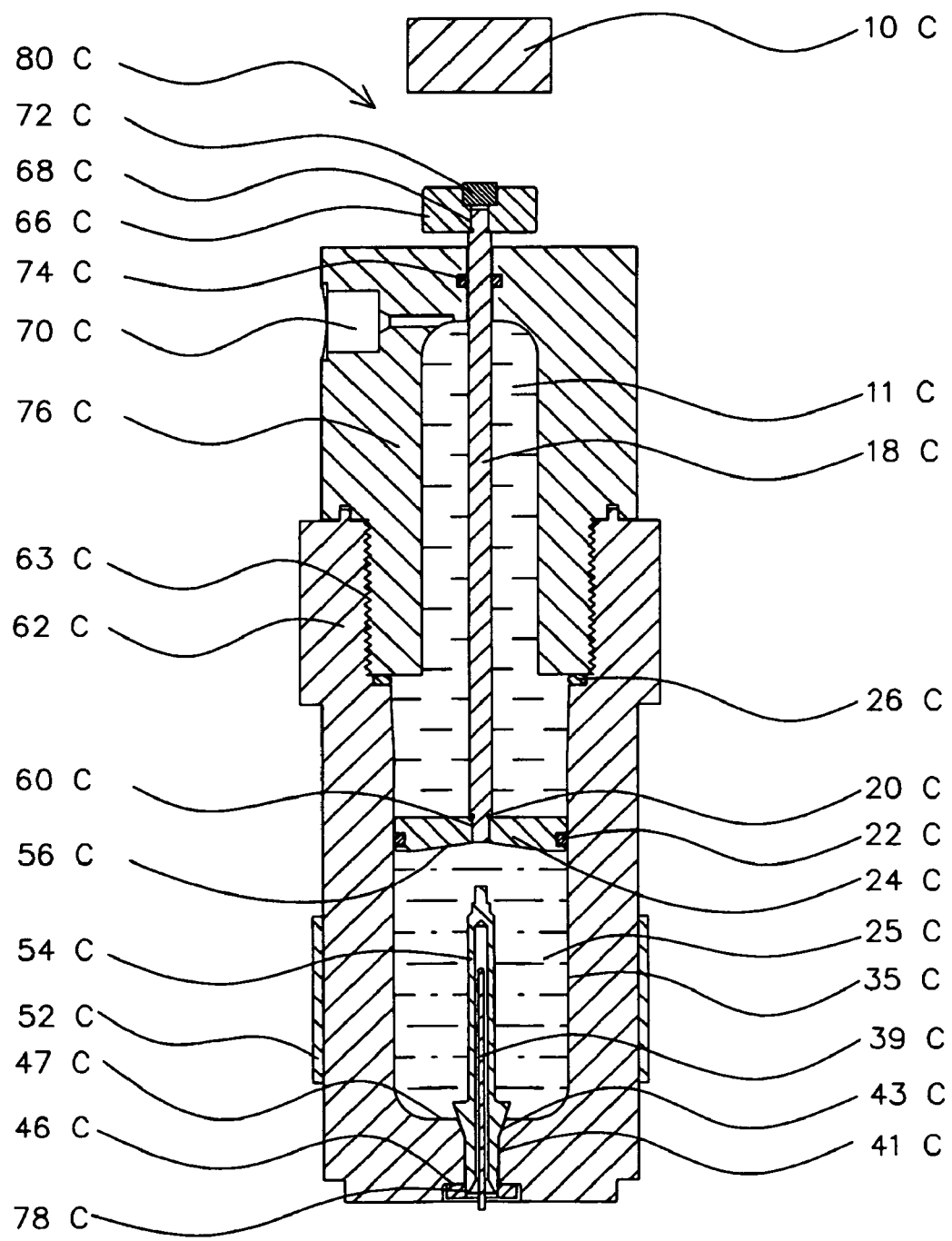
FIG. 4 shows an alternative configuration of cell assembly 80C where the top magnet is placed outside the cell body.

Description—FIG. 4—An Alternative Cell Assembly Embodiment with Top Magnet Outside Cell Body FIG. 4 is a cross-section view of a cell assembly 80C with a cell body 62C and a cell cap 76C. Cell body 62C is detachable from cell cap 76C via a screw thread 63C. An o-ring 26C assures against leakage through screw thread 63C. Inside of cell body 62C and below screw thread 63C is a cell wall 35C, which is cylindrical and extends downward to a cell bottom 47C. A tapered hole with a conical surface 43C and a straight bore 41C is located in the center of cell bottom 47C. Cell body 62C is mostly filled with a sample 25C. A pivot 54C, which is secured to cell bottom 47C by a lock nut 46C via a thread 78C, is seated into said tapered hole on conical surface 43C. Lock nut 46C is tightened to provide initial seal on conical surface 43C between cell bottom 47C and pivot 54C. A thermal couple 39C is inserted into the center of pivot 54C.

A piston 24C is attached to the lower end of a rod 18C by a screw thread 60C, with a conical surface 56C facing down. An o-ring 22C is mounted onto piston 24C and an o-ring 20C is mounted onto rod 18C to assure against the mixing of sample 25C with a pressurization fluid 11C. The top of rod 18C extends through a hole in the center of the top of cell cap 76C, where it is attached to a magnet holder 66C by a screw thread 68C. An o-ring 74C assures against the leakage of pressurization fluid 11C.

A magnetometer 10C is positioned above the top of cell assembly 80C. A top magnet 72C is placed at the top of magnet holder 66C. A pressurization port 70C is provided to supply pressurization fluid 11C to the top of piston 24C. A heater 52C heats cell body 62C while thermal couple 39C provides temperature feedback for temperature control.

Operation—FIG. 4—An Alternative Cell Assembly Embodiment with Top Magnet Outside Cell Body In FIG. 1, place pivot 54C inside of cell body 62C so that straight bore 41C and conical surface 43C are secured to cell bottom 47C via thread 78C and lock nut 46C. Pivot 54C can be cleaned together with cell body 62C.

Pour sample 25C into cell body 62C so that the surface of sample 25C submerges the top of pivot 54C enough so that piston 24C has sufficient upward and downward movement range. Install o-ring 22C onto piston 24C and push piston 24C downward into cell body 62C. As piston 24C is pushed down, o-ring 22C forms a seal with cell wall 35C, and conical surface 56C at the bottom of piston 24C ensures the air is first funneled out through the center of piston 24C. Keep pushing down on piston 24C until sample 25C comes out at the center of piston 24C. Install o-ring 20C onto rod 18C above screw thread 60C, then screw rod 18C into piston 24C via screw thread 60C. Install o-ring 26C into cell body 62C.

Install o-ring 74C, then screw down cell cap 76C into cell body 62C via screw thread 63C, allowing the top of rod 18C to pass through the hole in the center of the top of cell cap 76C. Screw magnet holder 66C onto rod 18C via screw thread 68C. Attach top magnet 72C to magnet holder 66C. Heater 52C heats cell body 62C while thermal couple 39C provides temperature feedback for temperature control.

Pressurization fluid 11C is introduced into cell top chamber via pressurization port 70C, compressing sample 25C inside of cell body 62C through the movement of piston 24C.

The temperature and pressure conditions inside of the cell assembly 80C cause sample 25C density to change, which in turn moves piston 24C. Top magnet 72C moves with piston 24C. The movement of top magnet 72C is sensed by magnetometer 10C and translated to density change of sample 25C mathematically.

Ramifications

In FIG. 1, magnetometer 10 can be easily replaced with an ultrasonic sensor which can measure the movement of magnet holder 66 or piston 24 across cell cap 76 top wall. Furthermore, said ultrasonic sensor could also locate inside of cell assembly 80 with its wire sealed across cell cap 76 wall while sensing the movement of piston 24. Also said ultrasonic sensor could locate at top or bottom end of cell assembly 80.

In FIG. 2, magnetometer 10A can be easily replaced with an ultrasonic sensor which can measure the movement of piston 24A. Furthermore, said ultrasonic sensor could locate inside of or outside of cell assembly 80A. Also said ultrasonic sensor could locate at top or bottom end of cell assembly 80A.

In FIG. 1, magnetometer 10 can also be replaced by other kinds of non-contact movement measurement sensors as long as they can sense the movement of piston 24, such as a capacitance sensor, eddy current sensor, etc.

In FIG. 1, magnetometer 10 and top magnet 72 can also be replaced by a LVDT sensor set. This said LVDT sensor core is located inside of cell assembly 80 and moves with piston 24 while said LVDT coil is disposed outside of cell assembly 80 along its axial direction. Said LVDT coil can measure the movement of said LVDT sensor core.

In FIG. 2, magnetometer 10A and top magnet 72A can also be replaced by a LVDT sensor set. This said LVDT sensor core is piston 24A while said LVDT coil is disposed outside of cell assembly 80A along its axial direction. Said LVDT coil can measure the movement of piston 24A.

In FIG. 4, magnetometer 10C and top magnet 72C can also be replaced by a LVDT sensor set. This said LVDT sensor core moves with rod 18C while said LVDT coil can measure the movement of said LVDT sensor core.

In all configurations, stirring of sample is optional.

Pressurization fluid 11, Pressurization fluid 11A and Pressurization fluid 11B can be either gas or liquid as long as their pressure is controlled.

CONCLUSION, AND SCOPE

Accordingly, the reader skilled in the art will see that this invention can be used to construct a pivotal high pressure vessel in which fluid or solid sample can be tested under varying and controllable conditions of high pressure and high temperature conditions for density changes. In so doing, it satisfies an eminent drilling industry need.

Objects and Advantages

From the description above, a number of advantages of my densitometer become evident:

a. Sample fluids under high temperature and high pressure can be subjected to test conditions without contamination by pressurization fluid.
b. Due to limited number of components, current invention is easy to operate and maintain.
c. The pressure rating of current invention will only be limited to the pressure rating of its pressure vessel, tubing and valves, which can be up to 60,000 psi.
d. Current invention can test both fluids and solids dynamically and statically under high pressure and high temperature.

Further objects and advantages of my invention will become apparent from a consideration of the drawings and ensuing description.

What I claimed:

1. A volume measurement device comprising:
a) a pressure vessel,
b) within said pressure vessel a sealed movable piston, which divides said pressure vessel into a pressurization media chamber and a sample chamber, furthermore said sealed movable piston and any other parts that move together with said sealed movable piston are completely contained within said pressure vessel,
c) said pressurization media chamber is filled with a pressurization media,
d) said sample chamber is at least partially filled with a liquid,
e) means for controlling the pressure of said pressurization chamber,
f) means for measuring the movement of said sealed movable piston while not contacting it,
g) a heater to provide thermal control on said pressure vessel.

2. The volume measurement device of claim 1 wherein said means for measuring the movement of said sealed movable piston while not contacting it is an ultrasonic distance sensor located outside of said pressure vessel.

3. The volume measurement device of claim 1 wherein said means for measuring the movement of said sealed movable piston while not contacting it is an ultrasonic distance sensor located inside of said pressure vessel.

4. The volume measurement device of claim 1 wherein said means for measuring the movement of said sealed movable piston while not contacting it is a LVDT sensor.

5. The volume measurement device of claim 1 wherein said means for measuring the movement of said sealed movable piston while not contacting it is a capacitance distance sensor.

6. The volume measurement device of claim 1 wherein said means for measuring the movement of said sealed movable piston while not contacting it is an eddy current distance sensor.

7. The volume measurement device of claim 1 wherein said means for measuring the movement of said sealed movable piston while not contacting it further consists of a magnet that moves together with said sealed movable piston and a magnetometer located outside of said pressure vessel.

8. A volume measurement device comprising:
a) a pressure vessel,
b) within said pressure vessel a sealed movable piston, which divides said pressure vessel into a pressurization media chamber and a sample chamber, furthermore said sealed movable piston and any other parts that move together with said sealed movable piston are completely contained within said pressure vessel,
c) said pressurization media chamber is filled with a pressurization media,
d) said sample chamber is at least partially filled with a liquid,
e) means for controlling the pressure of said pressurization chamber,
f) means for measuring the movement of said sealed movable piston while not contacting it,
g) a stirrer located inside of said pressure vessel.

9. The volume measurement device of claim 8 wherein said means for measuring the movement of said sealed movable piston while not contacting it is an ultrasonic distance sensor.

10. The volume measurement device of claim 8 wherein said means for measuring the movement of said sealed movable piston while not contacting it is a LVDT sensor.

11. The volume measurement device of claim 8 wherein said means for measuring the movement of said sealed movable piston while not contacting it is a capacitance distance sensor.

12. The volume measurement device of claim 8 wherein said means for measuring the movement of said sealed movable piston while not contacting it is an eddy current distance sensor.

13. The volume measurement device of claim 8 wherein said means for measuring the movement of said sealed movable piston while not contacting it further consists of a magnet that moves together with said sealed movable piston and a magnetometer located outside of said pressure vessel.

14. A high pressure pycnometer comprising:
(a) a pressure vessel,
(b) within said pressure vessel a sealed movable piston divides said pressure vessel into as least a pressurization media chamber and a sample chamber,
(c) said pressurization media chamber is filled with a pressurization media,
(d) said sample chamber is at least initially filled with a fluid,
(e) means for controlling the pressure of said pressurization chamber,
(f) means for measuring the movement of said sealed movable piston while not contacting it.

15. The high pressure pycnometer of claim 14 wherein said means for measuring the movement of said sealed movable piston while not contacting it is located outside of said pressure vessel.

16. The high pressure pycnometer of claim 15 wherein said means for measuring the movement of said sealed movable piston while not contacting it is an ultrasonic distance sensor.

17. The high pressure pycnometer of claim 14 wherein said sample chamber is sealed within said pressure vessel and does not communicate materials with said pressure vessel outside during operation.

18. The high pressure pycnometer of claim 14 further consists of a heater for thermal control of said pressure vessel.

19. The high pressure pycnometer of claim 14 wherein said means for measuring the movement of said sealed movable piston while not contacting it further consists of a magnet that moves together with said sealed movable piston and a magnetometer located outside of said pressure vessel.

20. The high pressure pycnometer of claim 14 further consists of means for converting said movement of said sealed movable piston to density change of said liquid.

* * * * *